United States Patent [19]
Lacey et al.

[11] Patent Number: 5,638,178
[45] Date of Patent: Jun. 10, 1997

[54] IMAGING POLARIMETER DETECTOR FOR MEASUREMENT OF SMALL SPACINGS

[75] Inventors: Christopher A. Lacey; Kenneth H. Womack, both of San Diego, Calif.

[73] Assignee: Phase Metrics, San Diego, Calif.

[21] Appl. No.: 522,553

[22] Filed: Sep. 1, 1995

[51] Int. Cl.[6] .................................................. G01B 11/14
[52] U.S. Cl. ............................................. 356/369; 356/382
[58] Field of Search ...................................... 356/364, 367, 356/369, 382, 365, 225; 250/225

[56] References Cited

U.S. PATENT DOCUMENTS

| | | |
|---|---|---|
| 3,847,485 | 11/1974 | Zanoni . |
| 4,015,127 | 3/1977 | Sharkins . |
| 4,306,809 | 12/1981 | Azzam ................................. 356/369 |
| 4,593,368 | 6/1986 | Fridge et al. ......................... 356/357 |
| 4,826,321 | 5/1989 | Coates et al. . |
| 5,130,866 | 7/1992 | Klaassen et al. . |
| 5,202,860 | 4/1993 | Takashashi et al. . |
| 5,218,424 | 6/1993 | Somargren . |
| 5,247,493 | 9/1993 | Kime et al. . |
| 5,280,340 | 1/1994 | Lacey . |
| 5,311,287 | 5/1994 | Amer . |
| 5,335,066 | 8/1994 | Yamada et al. ....................... 366/369 |
| 5,343,293 | 8/1994 | Berger et al. . |
| 5,557,399 | 9/1996 | de Groot ............................... 356/357 |

OTHER PUBLICATIONS

Wallace et al "Flying Height Testing at Near Contact," *Data Storage*, Sep./Oct 1995, pp. 55–58.

"Division-of-Amplitude Photopolarimeer (DOAP) for the Simultaneous Measurement of all Four Stokes Parameters of Light", Optica Acta, vol. 29(5), 1982, pp. 491–494 (no month).

"Electric Fields Produced by the Progagation of Plane Coherent Electromagnetic Radiation in a Stratiated Medium", J. of Optical Society of America, vol. 58(3), Mar. 1968, pp. 380–390.

"Static Stokes Ellipsometer: General Analysis and Optimization", J. of Modern Optics, vol. 38(5), 1991, pp. 889–896 (no month).

*Primary Examiner*—Richard A. Rosenberger
*Attorney, Agent, or Firm*—Blakely Sokoloff Taylor & Zafman

[57] ABSTRACT

An apparatus and method for measuring the space between a transparent member such as a disk, and reflective member such as a slider, by detecting a change of polarization of a reflected light beam. The apparatus includes a light source that emits a light beam. The light beam is circularly polarized and directed onto the disk and reflected off of the interface between the disk and the slider. The reflected light beam is split into four separately polarized beams by a beam splitter/polarizer assembly. The four light beams have varying intensities that are measured by photodetectors. Stokes parameters are computed from electrical signals that are generated by the photodetectors. The Stokes parameters correlate to the change in polarization of the reflected light beam. Ellipsometric parameters delta and psi are computed from the Stokes parameters. The thickness of the space and the complex index of refraction (n and K) of the slider are computed from the delta and psi parameters, typically by computing two separate sets of ellipsometric parameters at two different spacing thicknesses.

28 Claims, 2 Drawing Sheets

IMAGING POLARIMETER DETECTOR FOR MEASUREMENT OF SMALL SPACINGS

BACKGROUND OF THE INVENTION

1. Field of the Invention

The present invention relates to an optical polarimeter for measuring the space between a transparent member and a reflective member.

2. Description of Related Art

Hard disk drives contain a magnetic transducer(s) that magnetizes a flat rotating disk. The magnetic transducer is typically assembled to a suspension arm as part of a head gimbal assembly (HGA) that is suspended from an actuator arm. The actuator arm has a motor that moves the slider across the disk surface. Rotation of the disk creates an airstream which lifts the slider off of the disk surface. The air bearing created by the rotating disk prevents the slider and disk material from structurally wearing. The thickness of the air bearing can vary depending upon the spring rate of the suspension arm, aerodynamic characteristics of the slider and other factors.

When mass producing hard disk drives, it is desirable to measure the air bearing for each HGA to insure that the air bearing thickness is within operational tolerances. Various optical systems have been developed to detect the microinch and submicroinch air bearing thicknesses typically created in hard disk drive units. The air bearing thickness can be measured in optical systems by inserting the suspension arm into a test unit which has a transparent glass substrate. A light beam is then directed through the glass substrate and onto the slider. The reflection of light from the slider and the substrate air bearing interface creates an interference pattern that is detected by a photodetector. The thickness of the air bearing is computed from the interference pattern. The light source and photodetector are typically at approximately normal incidence to the slider and transparent substrate.

Interferometric testers typically require a calibration procedure to determine the maxima and minima of the interference pattern. The maxima and minima may be determined by varying the air bearing thicknesses, either by changing the rotational speed of the disk, or by mechanically unloading the slider. Once the maxima and minima are known, the air bearing thickness associated with a given detector signal can be calculated from the known functional form of the multiple-beam interference.

It has been found that some slider designs do not produce a wide enough range of air bearing thicknesses in response to variations in disk speed to determine maxima and minima. Retraction by mechanically unloading the slider has also been found to introduce errors because of slider tilt. In addition, the rate of change of light intensity goes to zero when the air bearing thickness is varied through an interference minimum or maximum. Additionally, it has been found that the signal to noise ratio degrades as the slider approaches the minimum associated with slider to disk contact.

For these reasons, prior art interferometers, such as the Phase Metrics DFHT, incorporate multiple wavelengths, and corresponding multiple detectors for signal to noise ratio improvements and for coping with loss of flying height measurement sensitivity at spacings which correspond to interferometric maxima and minima. A second type of multiple wavelength tester was marketed by IBM under the trademark CRAMA. The CRAMA system uses a two dimensional detector array in combination with a least square fit computation process to recover phase and determine air bearing thickness at each pixel of the interferogram image.

U.S. Pat. No. 5,218,424 issued to Sommargren, discloses an interferometer that functions at an incident angle that is not normal to the substrate. The Sommargren tester generates two laterally displaced perpendicularly polarized coherent light beams that are directed through the glass substrate at Brewster's angle for the substrate-air interface. One of the polarized light beams is transmitted through the substrate and reflected off of the slider. The other beam is reflected from the glass-air bearing interface. The reflected polarized light beams are recombined and directed onto a two-dimensional photodetector array. The Sommargren system includes a phase shifter that shifts the phase of the polarized beams directed onto the substrate. The detector measures the relative phase difference between the light reflected from the slider and the substrate-air bearing interface. The air bearing thickness is proportional to the phase difference of the light beams.

The Sommargren technique is advantageous because a calibration technique is not required to detect the maxima and minima for an interference signal. Additionally, intensity sensitivity is uniform and does not approach zero at the maximum and minimum locations. Unfortunately the Sommargren system will not compensate for variations in the real index of refraction n and extinction coefficient k of the slider. These coefficients may vary from slider to slider and create inaccurate measurements. Additionally, the Sommargren technique is limited to operation at Brewster's angle. Finally, the Sommargren tester does not make an absolute measurement of spacing but requires some independent calibration to find a zero air gap. It would be desirable to provide a tester that can make an absolute spacing measurement, was not restricted to a specific angle and compensated for the varying optical properties of different sliders.

SUMMARY OF THE INVENTION

The present invention is an apparatus and method for measuring the space between a transparent member such as a disk, and reflective member such as a slider, by detecting a change of polarization of a reflected light beam. The apparatus includes a light source that emits a light beam. The light beam is circularly polarized and directed onto the disk and reflected off of the interface between the disk and the slider. The reflected light beam is split into four separately polarized beams by a beam splitter/polarizer assembly. The four light beams have varying intensities that are measured by photodetectors. Stokes parameters are computed from electrical signals that are generated by the photodetectors. The Stokes parameters correlate to the change in polarization of the reflected light beam. Ellipsometric parameters delta and psi are computed from the Stokes parameters. The thickness of the space and the complex index of refraction (n and K) of the slider are computed from the delta and psi parameters, typically by computing two separate sets of ellipsometric parameters at two different spacing thicknesses.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
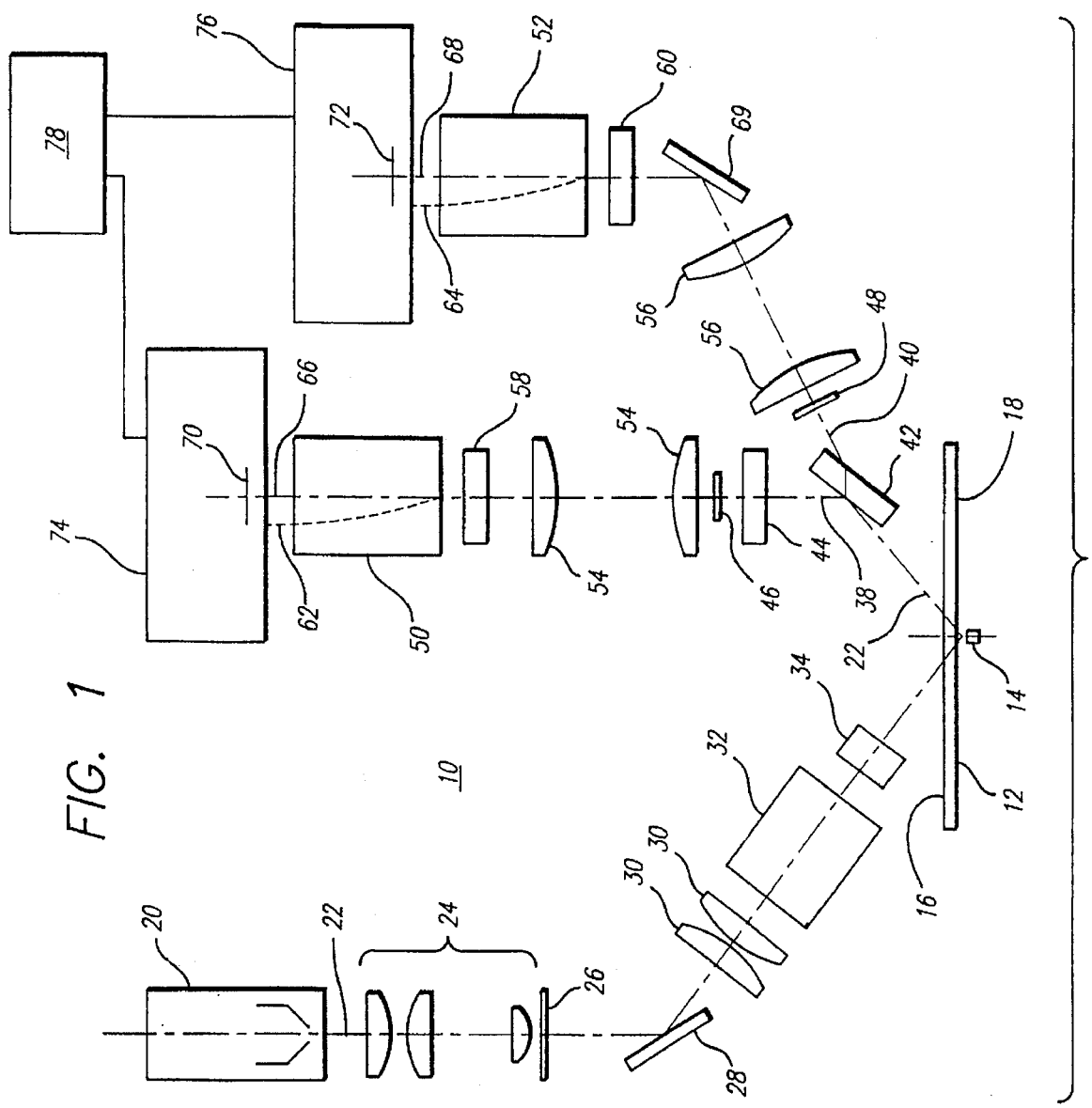
FIG. 1 is a schematic of a polarimeter detection system of the present invention.

Referring to the drawings more particularly by reference numbers, FIG. 1 shows a polarimeter detection system 10 of the present invention. The detection system 10 is used to measure the space between a transparent member 12 and a reflective member 14. The transparent member has a top surface 16 and a bottom surface 18.

The transparent member 12 is preferably a glass disk that is mounted to a motor (not shown) which can rotate the disk. The reflective member 14 is preferably a slider that contains a magnetic transducer which magnetizes and senses the magnetic field of a magnetic disk. The slider is typically mounted to a suspension arm (not shown). When the disk is rotated the airstream created by the rotating disk creates a pressure which pushes the slider away from the disk surface. The gap between the disk and slider is referred to as an air bearing. Although measuring the thickness of an air bearing of a hard disk drive assembly is shown and described, it is to be understood that the present invention can be used to determine the thickness of other substrates and layers.

The system 10 includes a light source 20 which emits a beam of light 22. In the preferred embodiment, the light source 20 is a Xenon arc strobe. The light beam 22 is directed through a condenser assembly 24 and an aperture 26. Because most slider designs are rectangular in shape it is desirable to have a rectangularly shaped aperture 26, although it is to be understood that the aperture 26 may have other shapes.

The light beam 22 is reflected by a mirror 28 into lenses 30. The lenses 30 focus the light beam 22 onto a small portion of the slider 14. The focused light should be preferably small enough to prevent interference between the light reflected from the slider 14 and light reflected from the top surface 16 of the disk 12.

The focused light beam goes through a crystal polarizer 32 and a quarter waveplate retarder 34. The polarizer 32 polarizes the light beam and the quarter waveplate 34 retards a polarized component to produce a circularly polarized light beam. Although a separate polarizer 32 and quarter waveplate 34 are shown and described, it is to be understood that other elements for circularly polarizing the light may be employed. Additionally, although circularly polarized light is discussed, the present invention may use a light beam polarized in another manner, such as 45° linearly polarized light.

Figure 2:
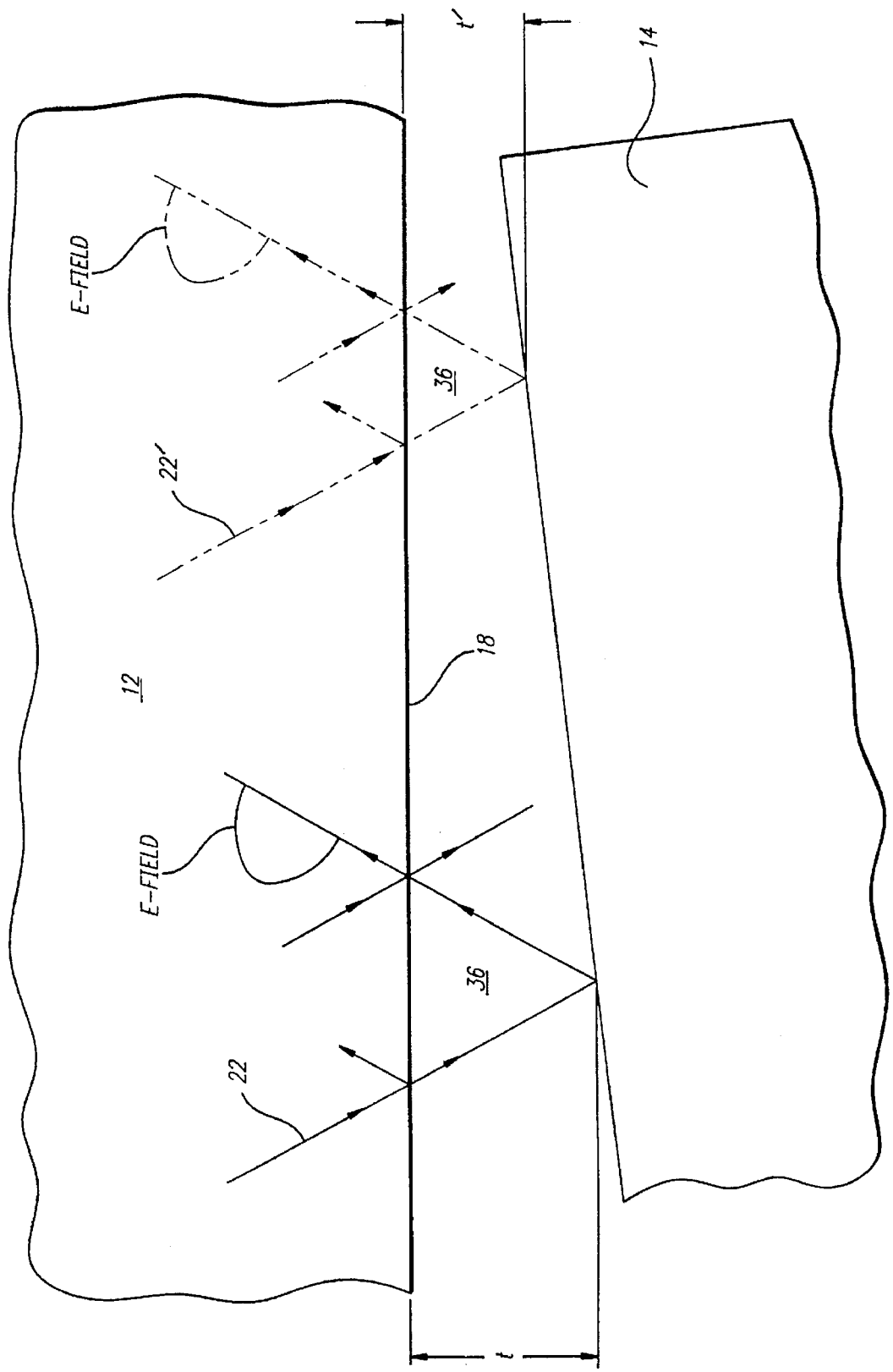
FIG. 2 is an enlarged view showing a light beam being reflected off of a slider-disk interface.

As shown in FIG. 2, the circularly polarized light beam 22 is directed onto the substrate 12. In the preferred embodiment the polarized light beam has an angle of incidence of approximately 60°. The light refracts through the substrate 12, and the space 36 between the bottom surface 18 of the substrate and the slider 14. The space 36 has a thickness of t. The light beam 22 then reflects off of the slider 14 and back through the space 36 and substrate 12. The slider 14 has a complex index of refraction which is the summation of the real index of refraction n and the extinction coefficient k.

When the light beam 22 reflects off of a slider 14 located at space thickness t' the reflected light has a certain E-field polarization shown in solid lines. When the light beam is reflected from a space thickness t' the optical path becomes longer, so that the phase of the polarized reflected light beam 22' is different, as indicated in phantom, than the reflected light beam 22. In general, the polarization of the light beam 22 will be a function of the space thickness and the optical properties of the substrate 12 and the slider 14. The varying space thickness t' can be created by varying the disk speed and the corresponding spacing of the air bearing, or by measuring a different point on the slider by analyzing a different group of pixels on the CCDs.

Referring to FIG. 1, the reflected light beam is split into two light beams 38 and 40 by a beam splitter 42 which reflects a portion of the reflected light and transmits a portion of the light. In the preferred embodiment, the beam splitter 42 is constructed from a BK-7 glass that has a coating of $TiO_2$ with an index of refraction of 2.35 and a thickness of 28.5+/−3 nm.

Beam 38 is reflected from the beam splitter 42 to substrate 44. The substrate emulates the transmissivity of the beam splitter 42 substrate. Both beams 38 and 40 travel through a pair of crystal quartz 45° polarization rotators 46 and 48. The polarization rotators 46 and 48 vary the polarization of the light beams 38 and 40 to orient the polarization vectors to optimize the usage of the polarization prisms 50 and 52.

The polarized light beams 38 and 40 are focused onto a pair of polarization displacement prisms 50 and 52 by lenses 54 and 56. The light beams are filtered by a pair of interference filters 58 and 60 before traveling into the prisms 50 and 52, respectively. In the preferred embodiment, the interference filters 58 and 60 have a bandwidth of 10 nm centered at 546 nm.

Each polarization displacement prism laterally displaces one polarization component of a polarized beam 38 and 40 from another polarization component of the polarized beam. The different polarized components define a pair of extraordinary beams 62 and 64 that are spatially displaced from a pair of ordinary beams 66 and 68, respectively. Each beam 62, 64, 66 and 68 will have a different polarization and typically a different corresponding light intensity than the other beams. Although the extraordinary beams 62 and 64 are shown, it is to be understood that the beams typically bend in a plane perpendicular to the paper. The beams are shown in the manner depicted in FIG. 1 for purposes of clarity. The displacement prisms 50 and 52 may be a Wollaston prism or any other birefringent polarizer. The size of the system 10 may be reduced by bending the beam 40 with a mirror 69.

The intensities of the light beams 62, 64, 66 and 68 are detected by charged coupled devices (CCD) 70 and 72 located within cameras 74 and 76. There is typically a separate CCD for each light beam 62, 64, 66 and 68. The CCD devices 70 and 72 convert the light energy of the beams 62, 64, 66 and 68 into electrical signals. The electrical signals are provided to a processor 78 that is coupled to the cameras 74 and 76.

The four beams 62, 64, 66 and 68 produce four electrical detection signals defined by the equation.

$$Ji=(J_1, J_2, J_3, J_4)^T$$

where;

$$Ji=CiIi$$

Ci=the sensitivity of the detectors.

Ii=the intensity of the light beams. From the detection signal the Stokes parameters Si representing the polarization of the light reflected from the slider can be computed with the following transformation matrix:

$$S_i = F^{-1} J_i$$

where;

$F^{-1}$=is a matrix characteristic of the polarimeter.

From the Stokes parameters the ellipsometric parameters delta ($\Delta$) and psi ($\psi$) can be calculated using the equations:

$$\tan\psi = \left[\frac{S_0 - S_1}{S_0 + S_1}\right]^{.5}$$

$$\tan\Delta = \frac{S_2}{S_3}$$

where;

$S_0$, $S_1$, $S_2$, $S_3$=the Stokes parameters.

The ellipsometric parameters delta $\Delta$ and psi $\psi$ are a function of the unknown space thickness t, the real index of refraction n, the extinction coefficient k of a given slider and other known optical parameters such as the index of the glass and air. Because there are two equations and three unknowns, it is preferably to measure the light intensities and compute the ellipsometric parameters for two separate space thicknesses t1 and t2. The measurements at each thickness t1 and t2 produce four known values; $\Delta 1$ $\Delta 2$, $\psi 1$ and $\psi 2$. The four known values are used to compute the four unknown values; t1, t2, n and k. The four unknowns values are preferably computed from the four known values using a Newton's method with numerical derivatives.

In the preferred embodiment it is desirable to limit the spacing to one periodic cycle. If the spacing is above one periodic cycle an integral number of periods can be added to the result to provide the correct spacing. More than two spacings can be simultaneously analyzed using a least squares or other technique to reduce the data for the overdetermined problem.

What is thus provided is an optical system for measuring the spacing of a thin layer or substrate without restricting the angle of incidence of the reflected light beam. Additionally, the present invention does not require the maxima and minima calibration steps typically found in interferometers of the prior art.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. For example, instead of splitting the reflected beam into four separately polarized beams, the reflected light beam could be directed into a rotating polarization retarder followed by a fixed polarizer. The intensity of the beam transmitted to the detector is changed at predetermined time intervals because of the rotation of the retarder. The light intensity of the beam may be measured at the different time intervals and used to compute the Stokes parameters and the corresponding t, n and k values of the glass-slider interface. In addition, instead of measuring delta and psi at multiple spacings, the ellipsometric parameters could be measured by using multiple angles of incidence, or multiple wavelengths of light to determine t, n and k. Furthermore, the system may contain only three separate photodetectors.

What is claimed is:

1. An apparatus for measuring a space between a transparent member and a reflective member, wherein the reflective member has a real index of refraction and an extinction coefficient, comprising:

a light source that directs a light beam through the transparent member and the space and onto the reflective member to simultaneously reflect off of a first point and a second point of the reflective member, wherein the light reflected from the first point has a first polarization and the light reflected from the second point has a second polarization;

a detector assembly that detects the first and second polarization of the reflected light; and, a processor that computes the real index of refraction, the extinction coefficient and the space from the first polarization and the second polarization of the reflected light.

2. The apparatus as recited in claim 1, wherein said detector assembly includes a beam splitter assembly that splits the first reflected light and the second reflected light into a first light beam, a second light beam, a third light beam and a fourth light beam that each have a different polarization and are detected by a photodetector assembly.

3. The apparatus as recited in claim 2, wherein said beam splitter assembly includes a beam splitter and a pair of polarization prisms.

4. The apparatus as recited in claim 3, wherein said detector assembly includes a pair of 45° degree polarization rotators.

5. The apparatus as recited in claim 2, wherein said processor computes a first stokes parameter, a second stokes parameter, a third stokes parameter and a fourth stokes parameter from the first, second, third and fourth light beams and then computes the real index of refraction, the extinction coefficient and the space from the first two pairs of ellipsometric parameters.

6. The apparatus as recited in claim 1, wherein said processor computes the real index of refraction, the extinction coefficient and the space from two sets of ellipsometric parameters.

7. A tester for measuring a space between a disk and a slider, wherein the slider has a real index of refraction and an extinction coefficient, comprising:

a light source that directs a light beam through the disk and the space and onto the slider to simultaneously reflect off of a first point and a second point of the slider, wherein the light reflected from the first point has a first polarization and the light reflected from the second point has a second polarization;

a detector assembly that detects the first and second polarization of the reflected light; and, a processor that computes the real index of refraction, the extinction coefficient and the space from the first polarization and the second polarization of the reflected light.

8. The tester as recited in claim 7, wherein said detector assembly includes a beam splitter assembly that splits the first reflected light and the second reflected light into a first light beam, a second light beam, a third light beam and a fourth light beam that each have a different polarization and are detected by a photodetector assembly.

9. The tester as recited in claim 8, wherein said beam splitter assembly includes a beam splitter and a pair of polarization prisms.

10. The tester as recited in claim 9, wherein said detector assembly includes a pair of 45° degree polarization rotators.

11. The tester as recited in claim 8, wherein said processor computes a first stokes parameter, a second stokes parameter, a third stokes parameter and a fourth stokes parameter from the first, second, third and fourth light beams and then computes the real index of refraction, the extinction coefficient and the space from the first two pairs of ellipsometric parameters.

12. The tester as recited in claim 7, wherein said processor computes the real index of refraction, the extinction coefficient and the space from two sets of ellipsometric parameters.

13. An apparatus for measuring a space between a transparent member and a reflective member, wherein the reflective member has a real index of refraction and extinction coefficient, comprising:

light means for directing a light beam through the transparent member and the space and onto the reflective member to simultaneously reflect off of a first point and a second point of the reflective member, wherein the light reflected from the first point has a first polarization and the light reflected from the second point has a second polarization;

detector means for detecting the first and second polarization of the reflected light; and, processor means for computing the real index of refraction, the extinction coefficient and the space from the first polarization and second polarization of the reflected light.

14. The apparatus as recited in claim 13, wherein said detector means includes beam splitter means for splitting the first reflected light and the second reflected light into a first light beam, a second light beam, a third light beam and a fourth light beam that each have a different polarization and are detected by a photodetector assembly.

15. The apparatus as recited in claim 14, wherein said beam splitter means includes a beam splitter and a pair of polarization prisms.

16. The apparatus as recited in claim 15, wherein said detector means includes a pair of 45° degree polarization rotators.

17. The apparatus as recited in claim 14, wherein said processor means computes a first stokes parameter, a second stokes parameter, a third stokes parameter and a first stokes parameter from the first, second, third and fourth light beams and then computes the real index of refraction, the extinction coefficient, and the space from the first two pairs of ellipsometric parameters.

18. The apparatus as recited in claim 13, wherein said processor means computes the real index of refraction, the extinction coefficient and the space from two sets of ellipsometric parameters.

19. A tester for measuring a space between a disk and a slider, wherein the slider has a real index of refraction and an extinction coefficient, comprising:

light means for directly a light beam through the disk and the space and onto the slider to simultaneously reflect off of a first point and a second point of the slider, wherein the light reflected from the first point has a first polarization and the light reflected from the second point has a second polarization;

detector means for detecting the first and second polarization of the reflected light; and, processor means for computing the real index of refraction, the extinction coefficient and the space form the first polarization and second polarization of the reflected light.

20. The tester as recited in claim 19, wherein said detector means includes beam splitter means for splitting the first reflected light and the second reflected light into a first light beam, a second light beam, a third light beam and a fourth light beam that each have a different polarization and are detected by a photodetector assembly.

21. The tester as recited in claim 20, wherein said beam splitter means includes a beam splitter and a pair of polarization prisms.

22. The tester as recited in claim 26, wherein said detector means includes a pair of 45° degree polarization rotators.

23. The tester as recited in claim 20, wherein said processor means computes a first stokes parameter, a second stokes parameter, a third stokes parameter and a fourth stokes parameter from the first, second, third and fourth light beams and then computes the real index of refraction, the extinction coefficient, and the space from the first two pairs of ellipsometric parameters.

24. The tester as recited in claim 19, wherein said processor means computes the real index of refraction, the extinction coefficient and the space from two sets of ellipsometric parameters.

25. A method for measuring a space between a transparent member and a reflective member, comprising the steps of:

a) directing a light beam through the transparent member and the space and onto the reflective member to simultaneously reflect off of a first point and a second point of the reflective member, wherein the light reflected from the first point has a first polarization and the light reflected from the second point has a second polarization;

b) detecting the first and second polarization of the reflected light;

c) computing the real index of refraction, the extinction coefficient and the space from the first polarization and the second polarization of the reflected light.

26. The method as recited in claim 25, further comprising the step of circularity polarizing the light beam before the light beam is directed onto the transparent member.

27. The method as recited in claim 25, further comprising the step of splitting the reflected light beam into four separately polarized light beams.

28. The method as recited in claim 27, further comprising the step of computing a first stokes parameter, a second stokes parameter, a third stokes parameter and a fourth stokes parameter from the first, second, third and fourth light beams computing the ellipsometric parameters from the first, second, third and fourth stokes parameters and then computing the index of refraction, the extinction coefficient and the space from the first, second, third and fourth stokes parameters.

* * * * *